(12) United States Patent
Haar et al.

(10) Patent No.: US 9,883,828 B2
(45) Date of Patent: Feb. 6, 2018

(54) TEST ELEMENT AND TEST SYSTEM FOR EXAMINING A BODY FLUID

(75) Inventors: Hans-Peter Haar, Wiesloch (DE); Hans List, Hesseneck-Kailbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 737 days.

(21) Appl. No.: 12/101,971

(22) Filed: Apr. 12, 2008

(65) Prior Publication Data
US 2008/0249435 A1 Oct. 9, 2008

Related U.S. Application Data

(63) Continuation of application No. PCT/EP2006/009945, filed on Oct. 15, 2006.

(30) Foreign Application Priority Data

Oct. 15, 2005 (EP) ..................... 05022535

(51) Int. Cl.
*A61B 5/00* (2006.01)
*A61B 5/157* (2006.01)
(Continued)

(52) U.S. Cl.
CPC ............ *A61B 5/157* (2013.01); *A61B 5/1459* (2013.01); *A61B 5/14532* (2013.01);
(Continued)

(58) Field of Classification Search
CPC . A61B 5/1411; A61B 5/14532; A61B 5/1459; A61B 5/6848; G01N 21/7703
(Continued)

(56) References Cited

U.S. PATENT DOCUMENTS 4,622,974 A 11/1986 Coleman et al.
6,032,059 A * 2/2000 Henning et al. .............. 600/584
(Continued)

FOREIGN PATENT DOCUMENTS

AU 55604/86 A 10/1987
DE 43 43 872 6/1995
(Continued)

OTHER PUBLICATIONS

Fujikura, Machine Translation of JP 2005-087613A, translated on Aug. 24, 2014, 14 pages.*
(Continued)

*Primary Examiner* — Max Hindenburg
*Assistant Examiner* — Jonathan M. Foreman
(74) *Attorney, Agent, or Firm* — Bose McKinney & Evans LLP (57) ABSTRACT

The invention relates to a test element as a single-use article for examining a body fluid, comprising a lancing member that can be inserted into a body part, a collecting area configured thereon for body fluid obtained by the lancing and at least one light guide for an optical measurement in the collecting area. The collecting area is formed by a collection recess of the lancing member which extends in the lancing direction and the light guide is integrated into the lancing member such that it is secure against displacement and the distal end thereof is arranged in a proximal measurement zone of the collection recess.

48 Claims, 4 Drawing Sheets

(51) Int. Cl.
    *A61B 5/145* (2006.01)
    *A61B 5/1459* (2006.01)
    *G01N 21/77* (2006.01)
    *A61B 5/15* (2006.01)
    *A61B 5/151* (2006.01)

(52) U.S. Cl.
    CPC .... *A61B 5/150022* (2013.01); *A61B 5/15151* (2013.01); *A61B 5/15163* (2013.01); *A61B 5/15174* (2013.01); *A61B 5/150419* (2013.01); *A61B 5/150435* (2013.01); *A61B 5/150511* (2013.01); *A61B 5/150519* (2013.01); *A61B 5/6848* (2013.01); *G01N 21/7703* (2013.01); *A61B 5/15107* (2013.01); *A61B 5/15115* (2013.01); *G01N 2021/7773* (2013.01)

(58) Field of Classification Search
    USPC .......................................................... 600/583
    See application file for complete search history.

(56) References Cited

U.S. PATENT DOCUMENTS

| | | | |
|---|---|---|---|
| 6,498,941 B1 * | 12/2002 | Jackson | A61B 5/14546 600/310 |
| 6,584,335 B1 | 6/2003 | Haar et al. | |
| 7,310,543 B2 * | 12/2007 | Smart | A61B 5/14532 600/345 |
| 7,682,318 B2 | 3/2010 | Alden et al. | |
| 8,052,618 B2 * | 11/2011 | Haar et al. | 600/583 |
| 8,114,029 B2 * | 2/2012 | List et al. | 600/583 |
| 8,251,922 B2 * | 8/2012 | List et al. | 600/583 |
| 8,298,159 B2 * | 10/2012 | Haar | 600/583 |
| 8,671,543 B2 * | 3/2014 | Haar | 600/583 |
| 2003/0083686 A1 | 5/2003 | Freeman et al. | |
| 2005/0059166 A1 | 3/2005 | Markes | |
| 2010/0168617 A1 * | 7/2010 | Fuerst et al. | 600/583 |
| 2012/0165698 A1 * | 6/2012 | Kuhr et al. | 600/583 |

FOREIGN PATENT DOCUMENTS

| | | |
|---|---|---|
| DE | 103 25 699 | 2/2005 |
| EP | 0 210 869 | 2/1987 |
| EP | 0 221 005 | 5/1987 |
| EP | 1 441 214 | 7/2007 |
| JP | 62-101226 | 5/1987 |
| JP | 2000-511068 A | 8/2000 |
| JP | 2004-245830 A | 9/2004 |
| JP | 2004-528936 A | 9/2004 |
| JP | 2005-087613 A | 4/2005 |
| WO | WO 86/01728 A2 | 3/1986 |
| WO | WO 97/42882 | 11/1997 |
| WO | WO 97/42886 | 11/1997 |
| WO | WO 01/48461 | 7/2001 |
| WO | WO 2004/107970 | 12/2004 |
| WO | WO 2004/110275 | 12/2004 |
| WO | WO 2005/084530 A2 | 9/2005 |
| WO | WO 2005/104949 | 11/2005 |

OTHER PUBLICATIONS

Author Unknown, 430/Research Disclosure, Mar. 2000: 43112, Testelemente for transmission measurements.

* cited by examiner

TEST ELEMENT AND TEST SYSTEM FOR EXAMINING A BODY FLUID

This application is a continuation application of International Application PCT/EP2006/009945, filed Oct. 15, 2006, which claims priority to EP 05 022 535.8, filed Oct. 15, 2005, which are hereby incorporated by reference in their entirety.

BACKGROUND

The invention relates to a single-use test element for examining a body fluid, comprising a lancing member that can prick a body part, a collecting area configured thereon for collecting body fluid obtained by the lancing, and at least one light guide for an optical measurement in the collecting area. The invention also relates to a test system for the use of such test elements.

In the case of blood sugar self-monitoring that is carried out several times daily as part of an insulin treatment, it is desirable to impose as few as possible handling steps on the affected person and, at the same time, to ensure a painless and reliable measurement. For reasons of hygiene, single-use articles are used for this monitoring, which, as a mass-produced article, should be produced as cheaply as possible. The conventional concepts envisage transport of blood fluid, which is usually removed from the finger tissue area by a lancet puncture, onto a separate sensory element, for example, in the form of a test strip, in order to then start the actual measurement.

In order to further integrate the system, a combined arrangement was proposed in DE 10 325 699 in which a light-conducting hollow fiber is arranged concentrically around a coaxially movable lancet. The hollow fiber has a reagent layer on a distal front end which is loaded with escaping blood when the lancet is inserted into the body part, while light from an analytical unit can be coupled into or out of the proximal end of the hollow fiber. In a complementary design, the system has a hollow cannula with a light guide that can be moved therein whose distal end that is arranged in the cannula opening is also coated with an analyte-specific reagent. In order to simplify the sampling, the end of the light guide is pushed out of the cannula opening after the lancing process until it protrudes beyond the opening and thus ensures a problem-free contact of the test field with the blood of the patient. However, an additional drive control is necessary for the relative movement of the lancing element and light guiding element, and a check whether the blood contact has been successful is not envisaged.

SUMMARY OF THE INVENTION

Embodiments of the present invention further improve the known systems, address the disadvantages of complicated sample transport, and reliably increase user friendliness.

These teachings are based on the idea of automatically collecting fluid in a short capillary collecting section in a manner that is substantially free of dead volume and to derive an optical measuring signal therefrom. Accordingly, in exemplary embodiments, the collecting area is formed by a collection recess of the lancing member which extends in the lancing direction, the light guide is integrated into the lancing member such that it is secure against displacement, and the distal end thereof is arranged in a proximal measuring or measurement zone of the collection recess. A (smallest possible) quantity of blood can be taken up in the collection recess so that there is no interference with the analysis by interfering tissue components in the puncture wound and/or by uncontrollable mechanical pressure loads. Integration is simplified with regard to the manufacturing process by incorporating the at least one light guide such that it is fixed in position or secured against displacement. The arrangement allows the success of the collecting process to be checked in the proximal measurement zone.

In order to ensure a reliable measurement, an advantageous embodiment provides that the distal end of the light guide forms a sensor for detecting body fluid which fills the collection recess. In order to ensure that the collecting volume is adequately filled, it is advantageous when the light guide detects contact with body fluid in the collection recess in the end phase of liquid uptake.

Alternatively, or in addition to optical detection, it is also possible that at least one electrode to which an electrical voltage can be applied is arranged in the area of the collection recess for detecting liquid contact or detecting an analyte. The electrode can be formed by an electrical conducting wire integrated into the lancing member.

A further improvement is achieved in that the light guide and/or the electrode generates a measurement signal for controlling the movement of the lancing member as a function of a detected body fluid contact.

According to an exemplary embodiment, a test field which responds to an analyte in the body fluid, and in particular, a test field that undergoes an irreversible chemical reaction, is arranged in the area of the distal end of the light guide. Further miniaturization can be achieved by providing the distal end face of the light guide with a test field for an analyte in the body fluid, which is preferably permanently applied as a reagent layer.

In order to further increase reliability when examining very small quantities that are not perceptible to the user, it is advantageous when at least two and preferably three separate light guides are integrated into the lancing member for a parallel measurement and the distal ends of the light guides are laterally spaced apart.

In order to achieve a robust assembly despite miniaturization, it is advantageous when the distal ends of the light guides are optically coupled via a carrier foil to a common test field, the test field being formed by a reagent layer applied to the free front side of the carrier foil that faces away from the light guides. A reflective optical path between the light guide ends that transmit and those that receive via the test field which is irradiated on the rear side is particularly advantageous for an optical measurement with a high signal quality. For this purpose, the thickness of the carrier foil should be 0.5 to 1.5 times the mutual distance between the midlines of neighboring light guides. Another improvement is achieved by means of the fact that the light guides, the carrier foil and the reagent layer have matching and substantially identical refractive indices. This can be optimized by means of the fact that a reagent layer of the test field contains reaction-neutral auxiliary substances, and in particular, salts such as sodium chloride which when dissolved in the body fluid adjust the refractive index of the reagent layer to the refractive index of the at least one light guide.

It is advantageous for the light guide to be detachably connected, preferably via optical plug connections, to an optical transmitting and/or receiving unit of a measuring device. This can be achieved by means of the fact that the lancing member can be coupled, e.g., in a form-locking manner, to a coupling unit of a lancing drive where the coupling unit has an optical or opto-electronic interface that can also be moved during the lancing movement for connecting the light guide to an analytical unit.

Another advantageous embodiment provides that the length of the collection recess in the lancing direction is such that the proximal end section of the collection recess remains outside the body part during the puncture such that in any case body contact with the test chemistry is avoided, and conversely, interfering cell components can be kept away.

In order to allow a rapid uptake of liquid and thus also to minimize pain sensation, it is advantageous when the collection recess has a volume of 1 to 100 nl, preferably of 5 to 50 nl. In this connection, it is advantageous when the collection recess forms a capillary for a capillary-active liquid uptake. Liquid uptake can be further improved when the collection recess is in the form of a slot that is open on at least one side and preferably on both sides.

It is advantageous for the positioning of the light guides when the collection recess has a proximal end section with a widened cross-section as a measuring zone.

The light guide is advantageously formed by an optical fiber or a fiber bundle. It is also conceivable that the light guide is formed by a section of the lancing member that is formed from a light-conducting material. For an optimized light transmission, it is advantageous when the proximal end of the light guide has a larger cross-sectional area than its distal end.

The production process can be simplified when the support made of plastic is molded onto the lancing member, e.g., by a two-component injection molding technique. Another variant that is advantageous for manufacturing provides that the lancing member is formed from several layers of a flat material and the light guide is preferably arranged in a holding groove between two layers of the flat material.

It is advantageous for a precise lancing process when the lancing member has a lancing body that is sharpened by grinding and/or hardened by a coating. Laser-optical material processing methods also come into consideration, and in particular, ablation processes for sharpening edges such as those that are also known for the manufacture of razor blades.

In order to improve the uptake of liquid, the collection recess can be provided with a hydrophilic coating.

An automatic collection process of a small but sufficient amount of body fluid obtained through a skin puncture can be achieved by means of the collection recess forming a capillary for an automatic filling with body fluid and the length of the capillary is several times its diameter. An arrangement in which the test field is aligned transversely to the longitudinal direction of the collection recess so that the body fluid flows "head-on" into the test field is particularly useful for analyzing microscopic amounts of fluid.

Another aspect of the invention concerns a test element as a single-use article for examining a body fluid, comprising a lancing member that can be inserted into a body part, a collecting area configured thereon for body fluid obtained by the lancing and at least one signal guide preferably configured as a light guide or electrical conductive path for an optical or electrochemical measurement in the collecting area, wherein the collecting area is formed by a capillary-active collection recess of the lancing member that is elongated in (extends along) the lancing direction, and the signal conductor is integrated into the lancing member and is coupled to a test field that reacts to an analyte in the body fluid, and the test field at least partially borders a capillary cross-section head-on against the outflowing body fluid in a proximal measuring zone of the collection recess. This arrangement allows the fluid to be transported by capillary force over a short flow path in order to ensure that no interfering substances such as cell components affect the measurement and the actual measuring process can be carried out in a device that is uncoupled from the lancing process without the test field initially impairing the liquid transport. This enables the measurement to be carried out on an extremely small volume of liquid at a defined time when the flow front of the body fluid impinges on the test field.

An advantageous constructional embodiment provides that the lancing member has an offset shaft or that the light guide or signal conductor is step-shaped so that the lancing member can be coupled in a first plane to a lancing drive and the signal conductor/light guide can be coupled in a second plane to a transmitting and/or receiving means.

The invention also relates to a test system for examining a body fluid, in particular blood, with a holder for at least one test element. The user convenience is increased by providing a plurality of test elements stored in a magazine.

It is advantageous for the measuring process when the test element can be driven by a lancing drive in a reciprocating lancing movement and when a transmitting and/or receiving means of an analytical unit can be coupled to the light guide or signal conductor of the test element during the lancing movement. This can be achieved by virtue of the transmitting and/or receiving means moving together with the test element, e.g., as integrated parts of a drive plunger, during the lancing movement.

Such test systems are preferably used in the form of a portable hand-held device for blood sugar determination or other near-patient monitoring, for example, for coagulation diagnostics.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The test elements 10 shown in the drawing can be used as single-use articles for a blood sugar measurement in a hand-held device 12 that is designed for them. For this purpose, the test elements 10 (FIG. 3) comprise a lancing member 14 that can be inserted into a body part in a lancing movement, a collecting area 16 configured thereon for collecting a blood sample obtained by the lancing and at least one light guide 18 for an optical measurement in the collecting area 16.

Figure 1:
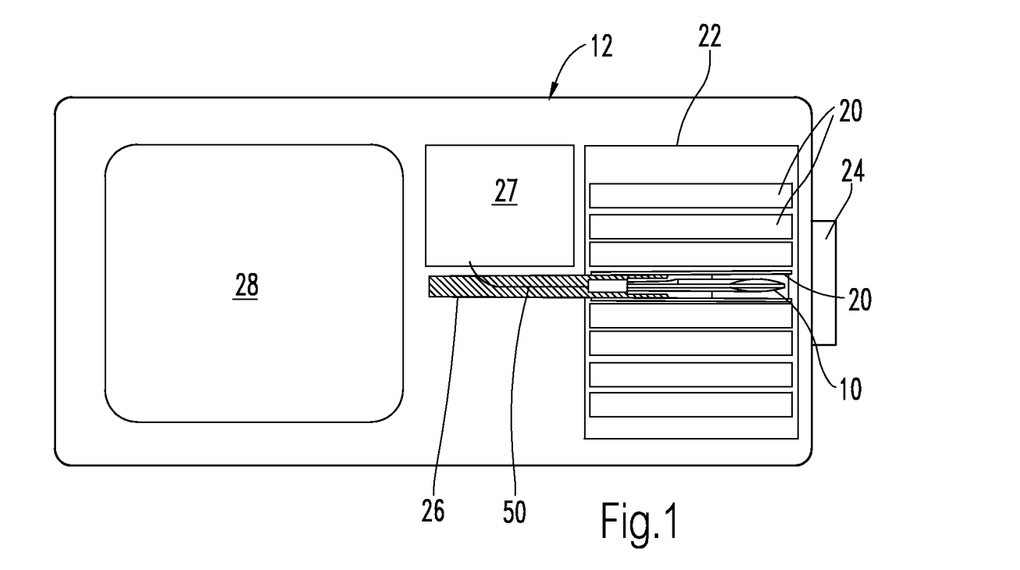
FIG. 1 is a diagrammatic view of a blood sugar measuring device.

As illustrated in FIG. 1, a plurality of test elements 10 in respective magazine chambers 20 of a stack-shaped or drum-like magazine 22 can be moved successively into an active position of use relative to a support 24 provided with a lancing opening for positioning the finger of a user. A lancing drive 26 which engages in the magazine chamber 20 enables in this connection a reciprocating movement of the lancing member 14 along a lancing axis or in a lancing direction. Blood is then collected in the collecting area 16 when the lancing member 14 is positioned in a collecting position of the lancing member 14, which is, optionally, slightly pulled back in the body part.

Figure 2:
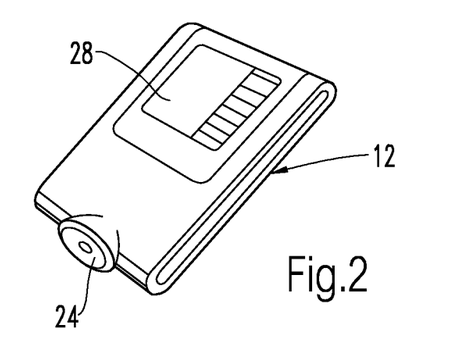
FIG. 2 is a perspective view of the device of FIG. 1.

The successful collection of blood and/or the content of an analyte (glucose) therein can be detected in situ in a very small volume by means of the light guide 18 without requiring large transport distances and dead volumes. Analysis and display of the current blood glucose level is possible by means of a microprocessor-assisted processing unit 27 and output unit 28. According to FIG. 2, all instrument functions are realized in a compact battery-driven hand-held device so that even laymen can determine their blood sugar concentration in a fully automated measuring process with a high degree of handling convenience.

In general, such measurements can also be carried out on other parts of the body, for example, the less pain-sensitive arm or abdominal region, in which case, apart from capillary blood from the skin, tissue fluid or mixtures thereof are also suitable as a body fluid for the sampling.

Figure 3:
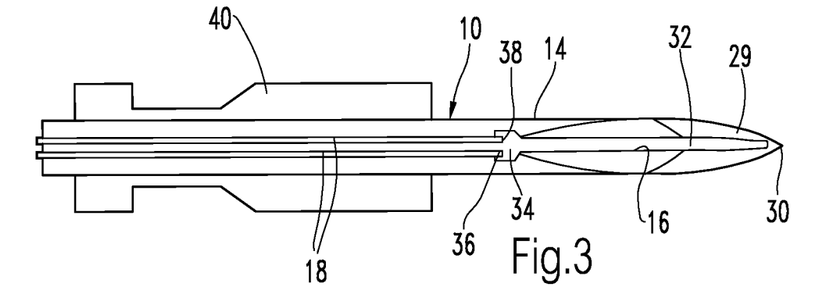
FIG. 3 is a side view of a test element provided with light guides.

FIG. 3 shows a single test element 10 with a shaft-like elongate lancing member 14 on the distal end of which a tip 30 sharpened by a ground section 29 is formed as a lancing body. The collecting area 16 is shaped as a longitudinal slot or recess (collection recess) 32 that is open on one or both sides and which as a capillary-active channel enables the transfer of a microscopic amount of sample into a proximal measuring zone 34 that is outside the skin. For this purpose, the length of the slot 32 is such that the measuring zone 34 still remains outside the body part even at the maximum penetration depth of the lancing body 30. At the same time, the elongate slit opening ensures an effective uptake of liquid without the risk of blockage by cell components. The lateral channel or recess opening thus advantageously extends over the length of the collecting area 16.

In order to make the blood withdrawal as gentle and as pain-free as possible, the volume of the collecting area 16 is only a few tens of nanoliters. In this connection, it is advantageous when it is ensured that liquid essentially only reaches areas where it is required, which can be accomplished by hydrophilically coating the collecting area 16 and, optionally, hydrophobizing the adjoining areas. The various hydrophilic and hydrophobic areas can, for example, be produced by applying the coating materials in a pad-printing process and/or also by photochemical functionalization.

It is also shown in FIG. 3 that two parallel light guides 18 are integrated into the lancing member 14 in a fixed manner so that the distal ends of the light guides 36 are laterally spaced apart and protrude into the proximal measuring zone 34 of the collecting area 16 that has a widened cross-section. In general, it is desirable for an "online-detection" of successful blood collection that the light guide or light guides at least partially border the collecting area in the end area facing away from the body, i.e., proximal end area. Since only a few nanoliters of blood reach this end section, the reliability of the measurement is increased by double detection using the parallel light guides 18. This is particularly useful for the user because he not only obtains a measurement, but also, quality-assurance information can be derived from the comparison of the two measurements.

The light guides 18 can have a special functionality when the ends 36 are designed as sensors for detecting a successful filling of the collecting area 16. In particular, a signal can be derived from a change in the refractive index when liquid is contacted in the end phase of blood collection which would be useful for a variable control of the lancing movement in the sense of a completed collection process. Thus, a regular collecting interval of, for example, 0.1 s can also be extended to, for example, 1 s in individual cases in order to avoid having to unsuccessfully terminate the measurement. It is also possible for such a liquid contact to be detected by integrated electrical sensors, and in particular, by a wire electrode instead of a light guide (not shown).

The light guides 18 can be formed by a single fiber or a fiber bundle. A so-called pulled fiber whose proximal cross-section is smaller than its distal cross-section can also be used for this so that a good optical connection to a coupling site is ensured.

The faces of the distal ends 36 of the light guides 18 are coated with a reagent layer as a test field 38 in order to directly detect the analyte in the measuring zone 34. The test chemistry as a known enzymatic system can be immobilized by polymerization on the end of the light guide so that it irreversibly reacts with blood glucose while changing its color. Scattering particles within the chemistry system enable an optical detection on the instrument side by scattering back the measuring light beamed in via the light guides 18.

The test element 10 is provided with a base member 40 which carries the lancing member 14 for a form-fitting drive coupling. This can be composed of plastic and can be molded onto the metallic lancing member 14 in a two-component injection-molding process. However, it is also conceivable that the lancing member 14 is also made of plastic and is additionally hardened in the area of the lancing body, for example, by a diamond-like carbon coating.

Figure 4:
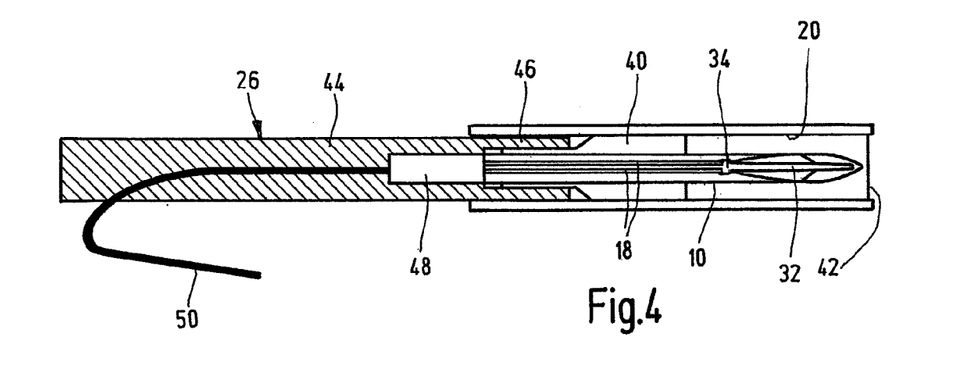
FIG. 4 is a side view of the test element of FIG. 3 coupled to a lancing drive.

As shown in FIG. 4, the lancing element 10 is linearly guided by the base member 40 within its magazine chamber 20. A piercable sealing foil 42 at the end of the magazine chamber 20 protects against moisture and ensures sterile protection. During the lancing movement, the drive plunger 44 penetrates the facing sealing foil and its pincer-shaped end 46 engages the base member 40. In this process, the light guides 18 are detachably connected to an interface 48 arranged in the plunger 44, which is elucidated in more detail below. The interface 48 is connected to the processing unit 27 by a flexible lead 50 which can be carried along during the lancing movement so that a signal can be processed and evaluated in the processing unit.

The lancing process itself can comprise the following in a controlled movement profile: a rapid lancing phase, a comparably longer and (optionally) somewhat retracted dwelling or collecting phase and a rapid retraction phase. In this connection, it is possible that the detection is also accomplished by the light guides 18 and proceeds in several steps, i.e., that only a blood contact is detected during the collecting phase, whereas the actual analysis does not take place until later in the instrument 12 or only after the retraction phase. It is also conceivable that the blood sample collected in the slot 32 is transferred to a separate test field such as that described in more detail in EP Application No. 05019055.2. In this case, the light guides 18 would be solely used for detecting the blood contact.

Figure 5:
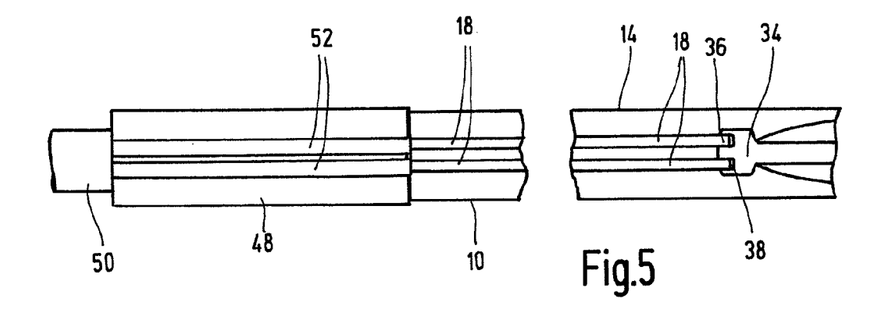
FIG. 5 is a fragmentary enlarged side sectional view of the test element and lancing drive shown in FIG. 4.

FIG. 5 shows an example of an optical interface 48 for coupling the test element 10 via an optical plug connection such as those that are, for example, known from telecommunication applications. In this case, proximal ends of the lights guides 18 of the test element 10 are in abutment and in contact with associated light guides 52 in the interface, which in turn are connected via the flexible lead 50 to a transmitter/receiver module fixed in the instrument. The mechanical tolerances of the plug connection should of course be low in order to obtain the required transmission quality for the measurement signal.

Figure 6:
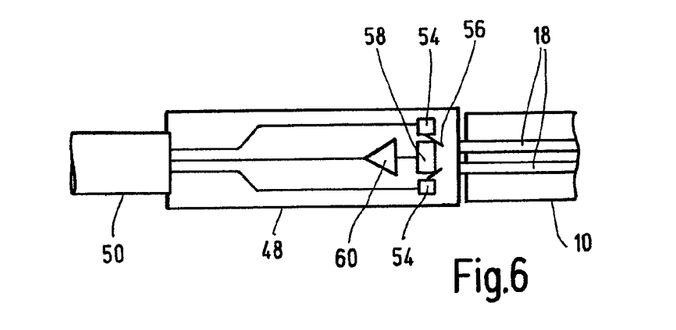
FIG. 6 is a fragmentary side view of a further embodiment of a coupling unit for the light guide.

In order to make the tolerance requirements less restrictive, it is possible to integrate an opto-electronic interface 48 into the lancing drive according to FIG. 6. Two electrically actuated LEDs 54 are provided as light emitters which are aligned onto the light guides 18 of the test element 10 via diaphragms 56. The light receiver is formed by a photodiode 58 that is screened by diaphragms 56 against crosstalk from the transmitter side, which is arranged after a preamplifier 60. This enables a robust electrical measurement signal to be transmitted from the interface 48 to the processing unit 27, where the interface is moved during the lancing process.

It is also possible to irradiate at different wavelengths using two LEDs in order to carry out different measurement tasks (e.g. detection of the test field wetting separately from the actual measurement).

Figure 7:
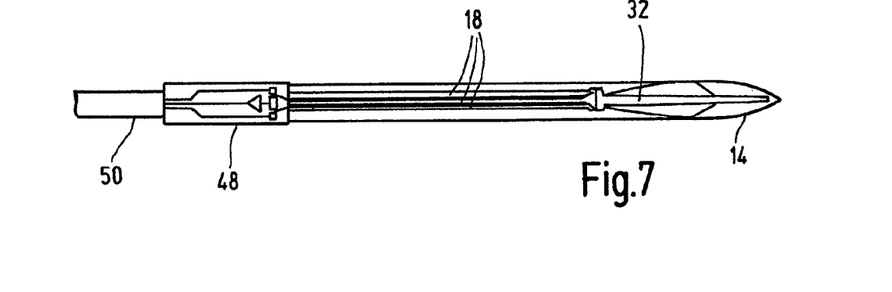
FIGS. 7 and 8 show further embodiments of a test element in side and enlarged sectional views.
Figure 8:
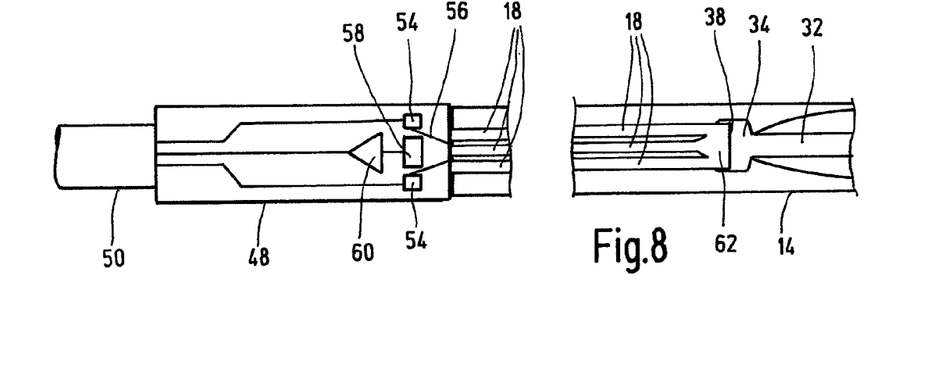

In the embodiment shown in FIGS. 7 and 8, three parallel light guides 18 are provided to further improve the decoupling between the transmitting and receiving side. At the coupling site, the two outer light guides for the transmitted light are completely screened from the receiver 58 by the diaphragms 56 which is thus only aligned with the exit cross-section of the middle light guide. In contrast, in the measuring zone 34 the light guides 18 end in a common end piece 62, the free end face of which is coated with the test chemistry. The receiving cross-section for the back-scattered light is optimized by the Y-shaped widening of the middle light guide relative to the test field 38. It would also be conceivable to replace the light-emitting diodes 54 in the interface 48 by light guides and only to carry out an opto-electronic conversion at the receiver side in the moved part.

For the optical measuring arrangement, the distal end sections of the light guides 18 are typically aligned perpendicular to the test field 38 and this test field is in turn aligned perpendicular or transversely to the flow direction of the body fluid in the collection recess 32.

Figure 9:
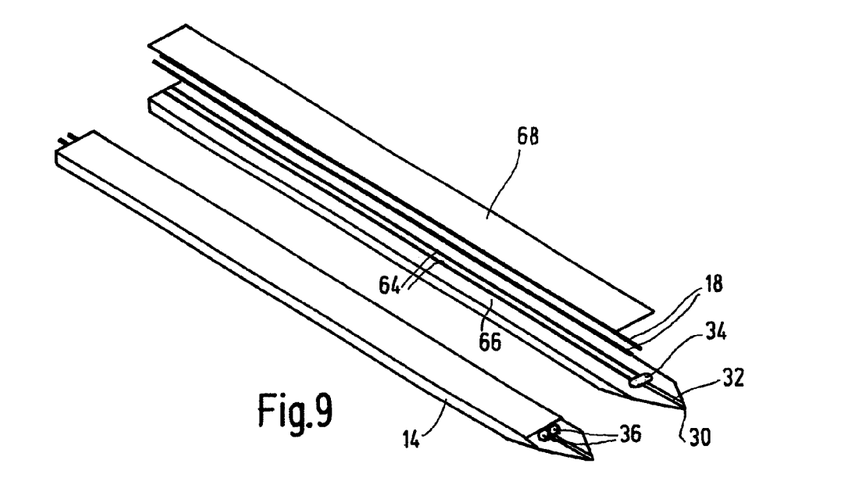
FIG. 9 is an exploded perspective view of a test element as a foil composite part.

FIG. 9 shows a variant of the lancing member 14 in the form of a composite body that is advantageous in production. In this case the light guides 18 can be inserted into receiving grooves 64 of a lancet member 66. The lancet member 66 can be made of high-grade steel sheet and the tip 30 can subsequently be provided with the recess 32 and the measuring zone 34 that is extended as a cut-out. The light guides 18 are fixed by a cover foil 68 which is laminated onto the lancet member 66.

Figure 10:
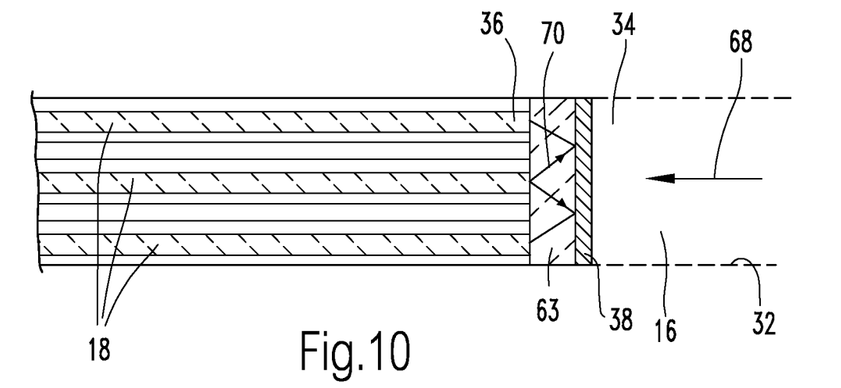
FIG. 10 is a sectional view of a longitudinal section through a test element in the area of the measurement detection at the collection recess.

FIG. 10 shows an embodiment similar to FIG. 8 with three parallel light guides 18 whose midlines or optical axes are aligned substantially perpendicularly to the test field 38 at least with regard to their distal end sections. Optical coupling to the rear side of the test field takes place via a carrier foil 63 which is permanently connected to the ends of the light guides in order to substantially reduce reflection losses. For this purpose the carrier foil 63 has a refractive index which substantially matches that of the light guides 18, i.e., which deviates within a few percent. The reagent layer applied as a test field 38 to the free front side of the carrier foil 63 is also adjusted to have a uniform refractive index at the boundary layer to the carrier foil 63. This can be achieved by suitably adapting the refractive index in the reagent layer that is loaded with blood fluid by means of reaction-neutral additives, such as sodium chloride. In this connection, the wetting with blood takes place via the test field surface at a defined time, as soon as the fluid that is taken up distally in the capillary channel 32 impinges frontally on the test field, which proximally blocks at least one partial cross-section of the capillary channel due to the capillary-active transport in the flow direction 68. A short flow path is sufficient for this without requiring the blood to flow past a lateral measuring surface. This also allows the sensitive area of the test field to be reduced to the flow cross-section, so that only a very small amount of sample is necessary for the actual measuring process and the liquid transport to the measuring site is not impaired. The optical arrangement between the middle in-coupling light guide and the two lateral neighboring out-coupling light guides is selected such that a direct reflective optical path 70 is possible on the rear side of the test field via the carrier foil 63. For this purpose the thickness of the foil 63 should approximately correspond to the distance between the midlines of the neighboring light guides 18.

Figure 11:
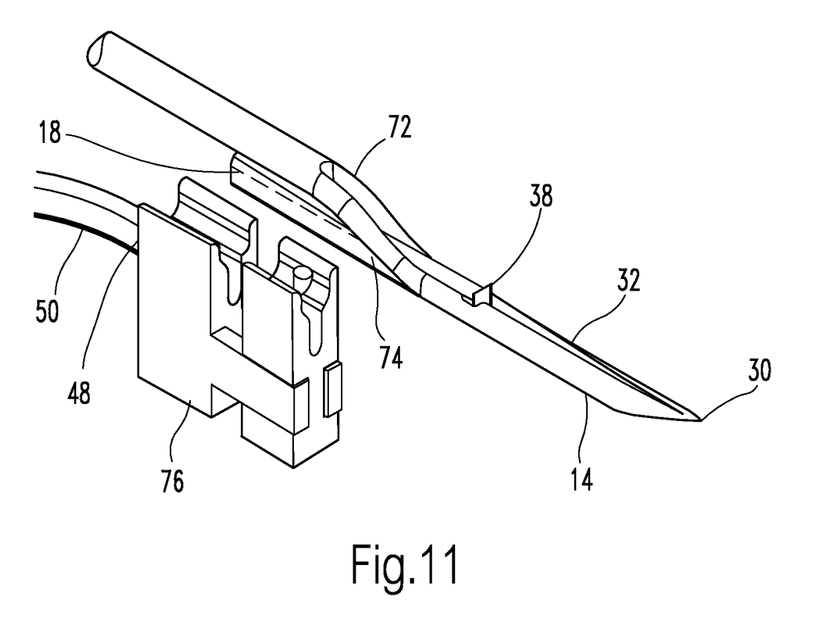
FIG. 11 is a perspective view of a further embodiment of a test element with an offset lancing member.

The embodiment according to FIG. 11 shows a lancing element 14 with an offset shaft 72 which has a slot in the region of the bend to receive a support 74 for the signal guides 18. This can be inserted together with the shaft 72 into an opto-mechanical holder 76 which allows it to be coupled to an optical or electrical interface 48. This creates two planes that preferably lie on top of one another, i.e., a first plane for the mechanical actuation of the lancing member 14 and a second plane for coupling the measurement signals in and out. This enables the construction to be simplified especially in the case of flat designs, for example, for use of a disk magazine from which relatively long lancing units 14 are ejected radially. It is also conceivable that a double plane for an advantageous coupling could be created by an offset lead carrier and a linear lancing shaft.

In this case as well as in the previously elucidated embodiment it is possible to provide electrical conducting paths instead of optical signal guides which in conjunction with reagent layer electrodes allow known electrochemical glucose measurements to be carried out in an optimized manner.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test system for examining a body fluid, comprising:
    a plurality of test elements for single use that are successively positionable in an active position for use, each test element comprising:
        a lancing member movable in a lancing direction and having a tip configured for insertion into a body part;
        a collecting area disposed in the lancing member and configured to collect body fluid obtained by lancing, the collecting area being shaped as an open longitudinal slot extending substantially in the lancing direction;
        a light guide integrated into the lancing member, the light guide having an end thereof protruding into the collecting area for an optical measurement; and
        a test field arranged at the end of the light guide, the test field aligned substantially transversely to the longitudinal direction of the slot, wherein the test field is configured to receive body fluid substantially head-on from the slot; and
    a lancet drive configured to drive the lancing member of each test element when positioned in the active position;
    wherein the light guide of each one of the plurality of test elements is detachably connectable to an optical transmitter or receiver.

2. The test element of claim 1, wherein the end of the light guide is configured for detecting body fluid.

3. The test element of claim 1, further comprising at least one electrode arranged about the collecting area.

4. The test element of claim 3, wherein the light guide or the at least one electrode is configured to generate a measurement signal for controlling the movement of the lancing member as a function of detected body fluid contact.

5. The test element of claim 1, wherein the light guide is configured to generate a measurement signal for controlling the movement of the lancing member as a function of detected body fluid contact.

6. The test element of claim 1, wherein the test field comprises a reagent layer for an analyte in the body fluid.

7. The test element of claim 1, wherein the light guide comprises two separate light guides integrated into the lancing member to provide a parallel measurement, the ends of the two separate light guides being spaced apart.

8. The test element of claim 7, further comprising a carrier foil that optically couples the distal ends of the light guides to a common test field, the common test field being formed by a reagent layer applied to a side of the carrier foil that faces away from the light guides.

9. The test element of claim 8, wherein the thickness of the carrier foil is about 0.5 to 1.5 times the distance between the midlines of the two separate light guides.

10. The test element of claim 9, wherein the light guides, the carrier foil and the reagent layer have substantially identical refractive indices.

11. The test element of claim 1, wherein a reagent layer of the test field contains reaction-neutral auxiliary substances configured to, when dissolved in the body fluid, adjust the refractive index of the reagent layer to substantially the same refractive index as the at least one light guide.

12. The test element of claim 1, wherein the light guide is detachably connectable to an optical transmitter or receiver of a measuring device.

13. The test element of claim 1, wherein the length of the collecting area in the lancing direction is configured such that a measurement zone of the collecting area remains outside the body part during the lancing.

14. The test element of claim 1, wherein the collecting area has a volume of 1 to 100 nl.

15. The test element of claim 1, wherein the collecting area has a volume of 5 to 50 nl.

16. The test element of claim 1, wherein the collecting area comprises a measurement zone at an end of the collecting area, the measurement zone having a widened cross-section.

17. The test element of claim 1, wherein the light guide comprises an optical fiber or a fiber bundle.

18. The test element of claim 1, wherein the light guide comprises a section of the lancing member that is formed from a light-conducting material.

19. The test element of claim 1, further comprising a plastic support molded onto the lancing member.

20. The test element of claim 1, wherein the lancing member is formed from at least two layers of a flat material and the light guide is arranged between the at least two layers of flat material.

21. The test element of claim 1, wherein the collecting area forms a capillary having a length several times its diameter.

22. The test element of claim 1, wherein one end of the collecting area is located near the tip of the lancing member and the other end of the collecting area terminates in a measurement zone, wherein the end of the light guide protrudes into the measurement zone.

23. The test element of claim 22, wherein the measurement zone has a widened cross-section.

24. The test element of claim 1, wherein the slot is open over the length of the collecting area.

25. The test element of claim 1, wherein the test element is configured to collect body fluid through the slot.

26. The test element of claim 1, wherein the slot forms a capillary configured to draw body fluid therein by capillary action.

27. A test system for examining a body fluid, comprising:
    a plurality of test elements for single use that are successively positionable in an active position for use, each test element comprising:
        a lancing member movable in a lancing direction and configured for insertion into a body part;
        a collecting area disposed in the lancing member and extending substantially in the lancing direction, the collecting area defining a capillary and being shaped as an open longitudinal slot extending substantially in the lancing direction;
        a signal conductor integrated into the lancing member; and
        a test field arranged on an end of the signal conductor and including a reagent configured to react with an analyte in a body fluid sample, the test field aligned substantially transversely to the longitudinal direction of the slot, the test field at least partially blocking the capillary in a measurement zone of the collecting area, wherein the test field is configured to receive flow of body fluid substantially head-on from the capillary; and
    a lancet drive configured to drive the lancing member of each test element when positioned in the active position;

wherein the signal conductor of each one of the plurality of test elements is detachably connectable to an optical transmitter or receiver.

28. The test element of claim 27, wherein the lancing member has an offset shaft or is step-shaped, wherein the lancing member is coupleable in a first plane to the lancing drive and the signal conductor is coupleable in a second plane to the transmitter or receiver.

29. The test element of claim 27, further comprising a carrier foil connected to the distal end of the signal conductor, the carrier foil coupling the signal conductor to the test field.

30. The test element of claim 29, wherein the refractive indices of the carrier foil, the signal conductor and the test field are substantially the same.

31. The test element of claim 27, wherein the signal conductor comprises two light guides that are spaced apart, the ends of the light guides at least partially bordering the measurement zone.

32. A test system for examining a body fluid, comprising:
a plurality of test elements for single use that are successively positionable in an active position for use, each test element comprising:
a lancing member movable in a lancing direction and configured for insertion into a body part;
a collecting area disposed in the lancing member and extending substantially in the lancing direction, the collecting area being shaped as an open slot extending substantially in the lancing direction and terminating in a measurement zone, the collecting area configured to collect body fluid obtained by lancing;
a light guide connected to the lancing member, the light guide being optically coupled to the measurement zone for an optical measurement; and
a test field arranged about the measurement zone, the test field substantially facing an end of the light guide and being arranged substantially transversely to the longitudinal direction of the collecting area; and
a lancet drive configured to drive the lancing member of each test element when positioned in the active position;
wherein the light guide of each one of the plurality of test elements is detachably connectable to an optical transmitter or receiver.

33. The test element of claim 32, further comprising a carrier foil connected to the distal end of the light guide, the carrier foil coupling the light guide to the test field.

34. The test element of claim 33, wherein the refractive indices of the carrier foil and the light guide are substantially the same.

35. The test element of claim 32, wherein the light guide comprises two light guides that are spaced apart and that are integrated into the lancing member.

36. The test element of claim 35, wherein the ends of the light guides at least partially border the measurement zone.

37. The test element of claim 32, wherein the end of the light guide is integrated into the lancing member and movable therewith.

38. The test element of claim 32, wherein the end of the light guide comprises a sensor for detecting body fluid which fills the collecting area.

39. The test element of claim 32, further comprising at least one electrode arranged about the collecting area, the at least one electrode configured to detect liquid contact or an analyte.

40. The test element of claim 32, wherein the test field comprises a reagent layer.

41. The test element of claim 32, wherein the end of the light guide is fixed to the lancing member.

42. The test element of claim 32, wherein the light guide is detachably connectable to an optical transmitter or receiver of a measuring device.

43. The test element of claim 32, wherein the measurement zone has a widened cross-section.

44. The test element of claim 32, wherein the light guide comprises an optical fiber or a fiber bundle.

45. The test element of claim 32, wherein the light guide comprises a section of the lancing member that is formed from a light-conducting material.

46. The test element of claim 32, further comprising a plastic support molded onto the lancing member.

47. The test element of claim 32, wherein the lancing member is formed from at least two layers of a flat material and the light guide is arranged between the at least two layers of flat material.

48. The test element of claim 32, wherein the collecting area forms a capillary having a length several times its diameter.

* * * * *